(12) United States Patent
Edvardsen et al.

(10) Patent No.: US 9,770,359 B2
(45) Date of Patent: Sep. 26, 2017

(54) OSTOMY BASE PLATE WITH MOULDABLE INNER ADHESIVE

(75) Inventors: Henrik Edvardsen, Copenhagen N (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 634 days.

(21) Appl. No.: 13/636,004

(22) PCT Filed: Mar. 18, 2011

(86) PCT No.: PCT/DK2011/050090
§ 371 (c)(1),
(2), (4) Date: Dec. 10, 2012

(87) PCT Pub. No.: WO2011/113442
PCT Pub. Date: Sep. 22, 2011

(65) Prior Publication Data
US 2013/0226116 A1 Aug. 29, 2013

(30) Foreign Application Priority Data

Mar. 19, 2010 (DK) .................................. 2010 70112

(51) Int. Cl.
*A61F 5/443* (2006.01)
*A61F 5/445* (2006.01)
(52) U.S. Cl.
CPC .............. *A61F 5/443* (2013.01); *A61F 5/445* (2013.01)
(58) Field of Classification Search
USPC ....................................................... 604/338
See application file for complete search history.

(56) References Cited

U.S. PATENT DOCUMENTS 4,701,169 A * 10/1987 Steer ...................... A61F 5/443
604/338
5,004,464 A * 4/1991 Leise, Jr. ................ A61F 5/445
604/338
(Continued)

FOREIGN PATENT DOCUMENTS

GB 2290974 A1 1/1996
RU 2220685 C1 1/2004
(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baurmann

(57) ABSTRACT

The current invention relates to a base plate (1) for an ostomy collection device, the base plate comprises at least one backing layer (3) whereon an outer adhesive layer (4) is disposed on the proximal side of said backing layer, wherein the outer adhesive layer encircles an inner adhesive layer (7) also disposed on the proximal side of at least one backing layer, said inner adhesive layer encircles a through-going hole (5) of the base plate defining a central axis A-A, wherein at least a part of the backing layer whereon the inner adhesive layer is disposed is extendable in a radial direction in respect to the central axis A-A. By allowing the backing layer to be radially extendable with the inner adhesive layer, the backing layer functions as a barrier to output from the stoma. Thus, output from the stoma will not come in direct contact with the distal side of the inner adhesive layer, which is shielded by the backing layer and thus extends the wear time of the ostomy appliance and reduces the risk that leakage may occur.

8 Claims, 2 Drawing Sheets

(56) References Cited

U.S. PATENT DOCUMENTS

| | | | | |
|---|---|---|---|---|
| 5,013,307 A * | 5/1991 | Broida | A61F 5/445 | 604/332 |
| 5,217,461 A | 6/1993 | Asher et al. | | |
| 5,718,696 A * | 2/1998 | Kollerup | A61F 5/443 | 604/332 |
| 5,722,965 A * | 3/1998 | Kuczynski | A61F 5/448 | 604/338 |
| 6,332,879 B1 * | 12/2001 | Nielsen | A61F 5/443 | 604/332 |
| 6,589,222 B1 * | 7/2003 | Olsen | A61F 5/443 | 604/336 |
| 6,626,878 B1 * | 9/2003 | Leisner | A61F 5/443 | 604/332 |
| 2003/0171737 A1 * | 9/2003 | Leise, Jr. | A61F 5/448 | 604/540 |
| 2006/0184145 A1 | 8/2006 | Ciok et al. | | |
| 2007/0027434 A1 * | 2/2007 | Pedersen | A61F 5/448 | 604/333 |
| 2009/0312685 A1 * | 12/2009 | Olsen | A61F 5/443 | 602/54 |
| 2010/0010542 A1 | 1/2010 | Jackson | | |
| 2010/0168693 A1 * | 7/2010 | Edvardsen | A61F 5/44 | 604/355 |
| 2010/0324511 A1 | 12/2010 | Dove et al. | | |
| 2012/0041404 A1 * | 2/2012 | Bach | A61F 5/443 | 604/344 |
| 2012/0302981 A1 * | 11/2012 | Lam | A61F 5/445 | 604/344 |
| 2013/0138065 A1 * | 5/2013 | Buus | A61F 5/443 | 604/344 |
| 2013/0226116 A1 * | 8/2013 | Edvardsen | A61F 5/445 | 604/338 |
| 2013/0226117 A1 * | 8/2013 | Hansen | A61F 5/448 | 604/338 |

FOREIGN PATENT DOCUMENTS

| | | |
|---|---|---|
| WO | 9817212 | 4/1998 |
| WO | 03020189 A1 | 3/2003 |
| WO | 2007076862 A1 | 7/2007 |
| WO | 2007121744 A1 | 11/2007 |
| WO | 2009/006901 | 1/2009 |
| WO | 2009021116 A2 | 2/2009 |
| WO | 2009021517 A1 | 2/2009 |
| WO | 2010060116 A1 | 5/2010 |
| WO | 2010/069334 | 6/2010 |
| WO | 10148182 A1 | 12/2010 |

* cited by examiner

OSTOMY BASE PLATE WITH MOULDABLE INNER ADHESIVE

TECHNICAL FIELD

The present invention relates to base plates for ostomy devices. In particular it relates to base plates having a mouldable centre for providing a tight fit of the base plate around the stoma of a user.

BACKGROUND

It is a common problem for ostomates that the skin area close to the stoma, also referred to as the peristomal area, is often irritated and sensitive. This is caused by stomal effluent, i.e. output from the stoma that runs back from the stoma opening, along the outer surface of the stoma and into contact with the peristomal skin area.

The output is very aggressive and quickly irritates the skin. Moreover, when the user is wearing a base plate for use in an ostomy device, either a one-piece or a two-piece device, then there is a high risk that the output running back from the stoma opening comes into contact with the inner edge of the adhesive of the plate. When in contact with the adhesive, the aggressive output will then erode the adhesive away.

In addition, seeing that sutures may have been used for securing the stoma during surgery or subsequent complications, the peristomal area may be scarred which makes it even more difficult to provide a seal between the skin and the adhesive wafer. This can create small gaps between the skin and the base plate where the output may enter, creating a moist environment that further irritates the skin but also deteriorates the adhesive attachment between the adhesive and the skin resulting in leakage or even dislodging of the base plate.

These problems have been addressed and tried solved in different ways.

WO 98/17212 discloses a separate sealing member disposed in the hole of the base plate. The sealing member is adaptable to the stoma without the use of tools.

US 2010/0324511 discloses an ostomy faceplate having a mouldable adhesive wafer.

Moreover, it is also important to provide a close fit between the through-going hole of the base plate and the stoma. This can for example be done by moulding a mouldable adhesive radially towards the stoma. In the known systems, this mouldable adhesive is left uncovered by the backing. This leaves the adhesive exposed and can be easily eroded by stomal output. Preventing erosion of the adhesive will significantly increase wear time of the base plate and also reduce the risk of leakage and unintentional detachment of the base plate.

Thus, there is still a need for a base plate which facilitates sealing around the stoma and which is able to provide protection of the peristomal area. In particular, there exists a need for a base plate where the mouldable adhesive is protected when it is moulded in a radial direction.

BRIEF DESCRIPTION

The invention relates to a base plate for an ostomy collection device, the base plate comprises at least one backing layer whereon an outer adhesive layer is disposed on the proximal side of said backing layer, wherein the outer adhesive layer encircles an inner adhesive layer also disposed on the proximal side of the at least one backing layer, said inner adhesive layer encircles a through-going hole of the base plate defining a central axis A-A, wherein at least a part of the backing layer whereon the inner adhesive layer is disposed is extendable in a radial direction in respect to the central axis A-A.

In use, the side of the base plate having the adhesive surface, forms the proximal side, that is the side which is attached to the skin of the user in such a way that the stoma extends through the through-going hole. The distal side of the base plate has a surface formed by the backing layer. The backing layer is typically a non-tacky material and covers the entire adhesive so that the garment and other accessories worn by the user do not stick to the base plate. The backing layer is also used as a support layer to handle the adhesive during production and also provides increased tear resistance to the base plate. In this description the terms 'proximal' and 'distal' are used to describe the relative position between parts and elements as they are arranged when the base plate is worn. Thus, the adhesive can be said to be proximal to the backing layer, since when worn, the adhesive is closer to the skin than the backing layer. Moreover, the adhesive has a proximal and distal surface. The distal surface is covered by the backing layer and the proximal surface of the adhesive can be covered by a release liner which is removed before use so that the base plate can be applied to the user when the proximal surface of the adhesive is pressed against the skin.

By providing a base plate as described it is possible to deform and shape the inner adhesive layer of the backing layer and thereby change the circumference of the through-going hole of the base plate. This advantageously provides an ostomy base plate where the adhesive surrounding the through-going hole can be shaped to closely follow the size and shape of the ostomy. This reduces the risk that output from the stoma comes between the adhesive of the base plate and the skin, thereby reducing the risk of leakage and scarring and irritating the skin.

Moreover, by allowing the backing layer to be radially extendable with the inner adhesive layer the backing layer functions as a barrier to output from the stoma. Thus, output from the stoma will not come in direct contact with the distal side of the inner adhesive layer, which is shielded by the backing layer. This means that the wear time of the ostomy appliance is extended and the risk that leakage may occur is reduced.

The feature that the backing layer is extendable in the radial direction should be read broadly within the current description as will be understood herein. For example, only parts of it has to be extendable or displaceable. Thus, in one embodiment the backing layer can initially be folded, wrinkled or otherwise pressed or collapsed together, for example by using embossment or grooves as described herein. In this context the feature that the backing layer is extendable in the radial direction covers that the backing layer is unfolded or expanded. In other embodiments, the backing layer is plastically deformable and thus the material itself is deformable. Herein, the feature that the backing layer is extendable in the radial direction covers that the backing layer is spread or stretched in the radial direction.

Accordingly, the feature that the backing layer can be extended in the radial direction encompasses embodiments where the backing layer may follow the radial deformation of the inner adhesive layer in the radial direction, without substantially limiting the movement of this adhesive layer.

The inner adhesive layer is preferably formed of a so called mouldable adhesive or sealing paste. Mouldable adhesives are generally characterised in that they can be moulded to a desired shape by using the fingers, and that it will basically remain in that shape after moulding. Mouldable adhesives are also often very compliant, i.e. they will take shape after the surface whereon they are applied allowing the adhesive to fit closely around scar tissue and other irregularities of the body and/or the peristomal skin surface, thereby providing a tight fit which reduces the risk of leakage.

When evaluating mouldable adhesives in more specific terms the parameters complex shear modulus |G*| and the tan(δ) within a frequency range can be used as good indicators of when an adhesive is mouldable. These parameters are typically determined by deforming the material under rotational shear deformation to 1% controlled deformation at 32° C. by using an oscillating frequency sweep.

The frequency range of interest is from 0.1 HZ-1 HZ as this is the frequency range in which handling of ostomy devices, such as application, wear and removal typically occur.

The complex shear modulus |G*| indicates the moulding characteristics of the adhesive, i.e. how easy it is to shape and manipulate it with for example your fingers. For mouldable adhesives the modulus is less than 250.000 Pa at 1 Hz, preferably the modulus |G*| is between 3.600 Pa to 36.000 Pa at 1 Hz.

The tan(δ) of an adhesive is a relation between the adhesive's elastic properties and its plastic properties. The higher the elastic properties of an adhesive, the more closely it will return to its original shape after it has been deformed, whereas if the plastic properties are high the adhesive will remain closer to its deformed state. When tan(δ)=1 the elastic and plastic properties are balanced. If tan(δ) is above 1, then the plastic properties are predominant and if tan(δ) is below 1 then the elastic properties are predominant. An adhesive will typically be considered mouldable if tan(δ) is above 0.9, most commonly it will have a tan(δ) above 1 or preferably 1.25.

A mouldable adhesive is for example described in the international published application WO 2010/069334, where it also is described how |G*| and tan(δ) are determined by using DMA (Dynamic Mechanical Analysis). This disclosure describes how to provide a mouldable adhesive which has a |G*| below 250.000 Pa and a tan(δ) above 0.9.

The outer adhesive layer is typically formed of skin-friendly adhesive. Such adhesive can for example be hydrocolloids based as typically used in ostomy appliances. Other suitable adhesives can for example be the modified hot melt adhesives such as described in WO2009/006901.

In one embodiment at least a part of the backing layer, whereon the inner adhesive layer is disposed, has a surplus of material allowing the backing layer and the inner adhesive layer to be displaced in a radial direction in respect to the central axis A-A.

In one embodiment such surplus of backing material can be provided by a backing material having a surface distance along the distal surface of the backing layer in the radial direction relative, between the outer and inner edge of the inner adhesive layer, and wherein this surface distance is larger than the radial extent of the inner adhesive, between the outer and inner edge of the inner adhesive layer. This can be formed as e.g. embossment in the backing layer whereon the inner adhesive layer is disposed.

Such embodiments are particularly advantageous when the backing layer is formed of a material which has a low stretchability or is otherwise difficult to deform. Such backing layers can for example be backing layers formed of a PU (polyurethane) or PP (polypropylene). Thus, the backing layer can still be displaced radially along with the inner adhesive layer due to the surplus of material.

In one embodiment, the inner area of the backing layer has an embossment. The embossment provides surplus of material that extends axially, i.e. transverse to the radial direction of which it is desired to extend the inner area of the backing layer.

The embossment may preferably be provided in an arrangement of at least one groove encircling the through-going hole.

Moreover, it can also be an advantage to use stiffer backing layers in cases where it is important that manufacturing is very exact because backing layers that are very stretchable and deformable can be difficult to handle during production.

In another embodiment a suitable backing layer can be chosen, wherein the part of the backing layer whereon the inner adhesive layer is disposed has a plasticity, which is equal to or larger than the plasticity of the inner adhesive layer.

Examples of backing layers having a high plasticity are films of polyethylene, polyethylene copolymers, polyurethane or blends of these materials preferably in a thickness of no more than 50 micron, preferably 15-35 microns.

In one embodiment, the inner adhesive layer is disposed on a backing layer different from the backing layer whereon the outer adhesive layer is disposed.

In one embodiment, the backing layer is capable of extension in the radial direction of 1 to 10 mm, preferably 3 to 6 mm. These are suitable extension dimensions which will fulfill most user needs.

In one aspect the description relates to a sealing wafer comprising a mouldable adhesive layer disposed on the proximal side of at least one backing layer, the mouldable adhesive layer encircles a through-going hole of the base plate defining a central axis A-A, wherein at least a part of the backing layer whereon the mouldable adhesive layer is disposed is extendable in a radial direction in respect to the central axis A-A.

Such sealing wafer can be a separate unit adapted to be arranged in an ostomy device, or it can be integrated therein as described in the following description.

DETAILED DESCRIPTION

Figure 1:
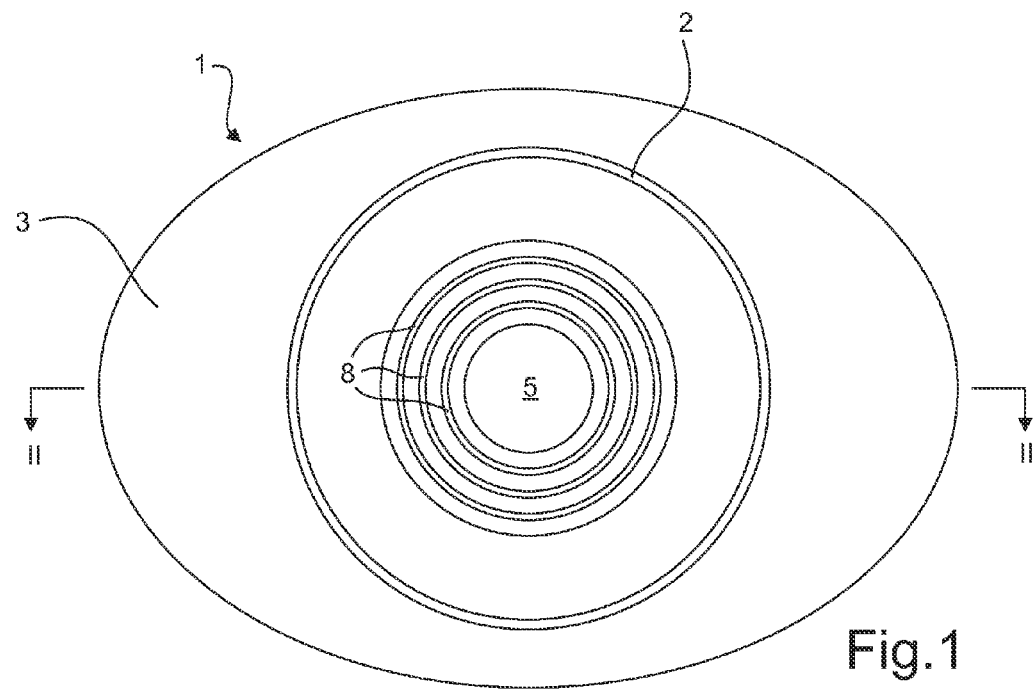
FIG. 1 shows in perspective the distal side of a base plate as described herein.

One embodiment of a base plate 1 is shown in FIG. 1-4. The base plate is for use in a two-piece mechanical ostomy device (not shown), where the coupling ring 2 is adapted to be coupled with a corresponding coupling ring (not shown) on a collecting bag (not shown). It should be understood that the present invention can be applied to other ostomy devices too, such as two-piece adhesive coupling devices or one-piece devices.

The base plate 1 has an annular shape and is formed of a backing layer 3 whereon an adhesive layer 4 is disposed. The backing layer can be for example, a polyurethane film which is commonly used as a backing layer in a base plate for ostomy devices. A through-going hole 5 extends axially A-A through the base plate.

The adhesive layer 4 is formed of an outer skin-friendly adhesive 6 which encircles an inner mouldable adhesive 7, which encircles and defines the through-going hole 5.

Three annular grooves 8 are formed in an inner area of the backing, whereon the mouldable adhesive is disposed. The grooves provide a surplus of material which allows the inner area of the base plate to be extendable in a radial direction. This allows the backing layer to follow the inner mouldable adhesive 7 as the user moulds the through-going hole into a size and shape that fits the specific size of the user's stoma as will be described.

Figure 2:
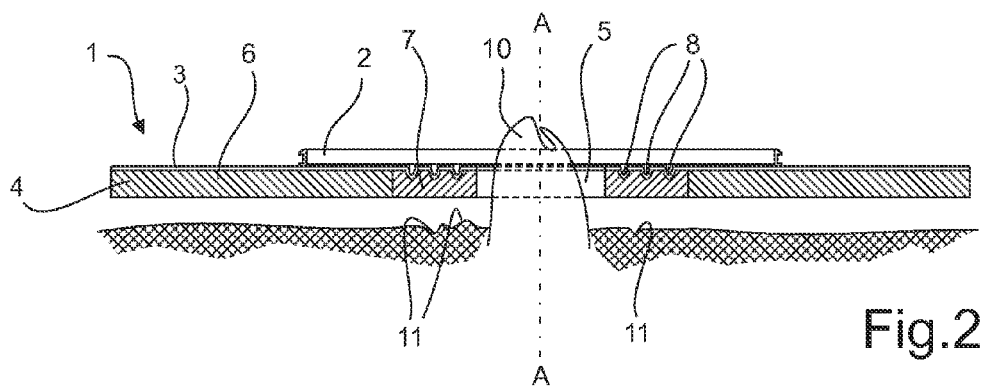
FIG. 2 shows the above in section along line II-II in FIG. 1, and FIGS. 3 and 4 show the above embodiment of the invention when applied to the user.

FIG. 2 further shows a stoma 10 which is received by the through-going hole 5. Scar tissue, wounds and/or blister (commonly referred to by the number 11) often creates crater-like formations 11 in the peristomal area, i.e. the skin area immediately surrounding the stoma. It is common that scars occur after surgery, or from wounds and blister caused by the stomal output that comes into contact and irritates the skin. The skin area outside the peristomal area is typically more even and curves naturally with the general body curvature.

Figure 3:
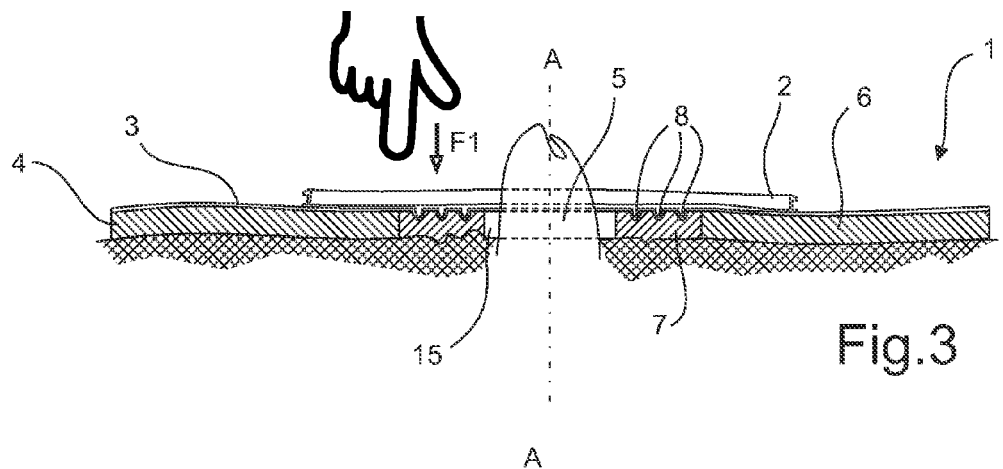

When initially applied to the skin as shown in FIG. 3, the base plate is pressed against the skin, i.e. a pressure along the axis A-A is provided as indicated by arrow $F_1$. Seeing that the outer skin-friendly adhesive and the inner mouldable adhesive in the current embodiment are so-called pressure sensitive they react to this pressure by adhering to the skin.

Moreover, the inner mouldable adhesive which has a relatively high plasticity will take shape of the contour of the peristomal area, and due to its plasticity and viscosity it will be able to fill out small spaces and around skin folds caused by e.g. scar tissue. The outer skin-friendly adhesive, although not having the same plasticity as the mouldable adhesive, is still flexible and will be able to follow the general curvature of the body which curves at a much lower frequency than e.g. scar tissue.

The mouldable adhesive provides a seal between the skin and base plate so that output from the stoma that may flow back into the through-going hole between the edge of the inner adhesive and the stoma, does not seep into small cracks between scar tissue and the adhesive. This could lead to initial separation of the base plate from the skin which in turn may cause leakage and eventually unintentional detachment of the base plate.

Figure 4:
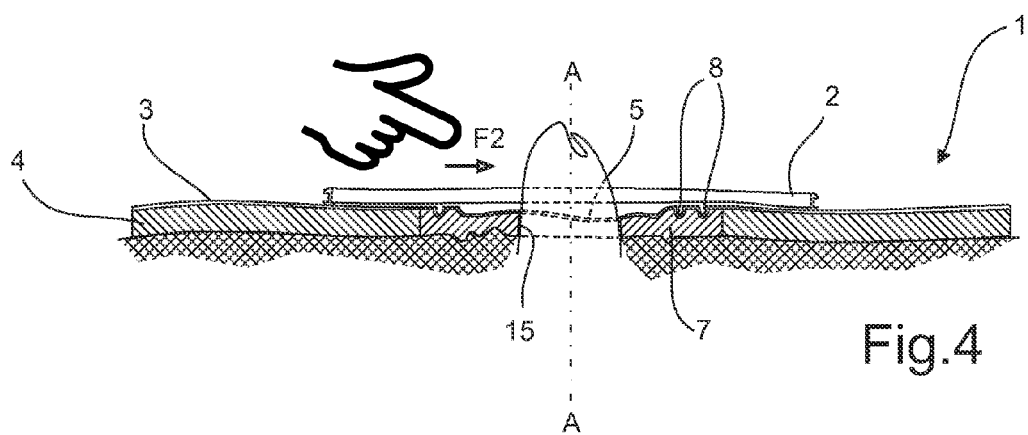

In order to reduce the amount of output that enters into the gap between the edge of the inner adhesive and the stoma, the inner adhesive may be moulded radially towards the stoma thereby reducing or even closing the gap. As shown in FIG. 4, the gap 15 is almost eliminated by moulding the mouldable adhesive 7 in a radial direction towards the central axis A-A of the through-going hole as indicated by arrow $F_2$. Moreover, seeing that the surplus of the backing layer material created by the grooves 8, the backing layer 3 can follow the radial extension of the mouldable adhesive and thus provide a protective barrier, which protects the distal side of the adhesive from stomal output.

Thus, in order to allow sufficient movement of the adhesive to shape and move freely when using a top film or a backing layer that is less plastic than the mouldable adhesive (as described in the current embodiment), the top film can be embossed. The embossment creates a surplus of film and the adhesive can more easily be extended radially by the user during application.

Moreover, ostomy base plates in the market can also be found with top films that are more elastic and plastic than the adhesive that they protect. However, with pastes, mouldable rings or shapeable adhesives it can be difficult to find a film that allows for radial extension of the adhesive once that adhesive has been applied to the skin. This can be aided by creating a surplus of material, both film and adhesive, using embossment technology as described.

In many cases where a soft mouldable adhesive needs to be protected, an easily stretchable top film like a thermoplastic polyurethane (TPU) could be considered. However, though easily stretched, the TPU tends to contract immediately after being elongated; this will also stress the adhesive and cause it to return to its original position just like the top film.

Thus, by using an embossment pattern the radial extension of a shapeable adhesive can more easily be controlled.

The desired effect of the embossment is an extension towards the stoma of 1 to 10 mm, preferably 3 to 6 mm.

The embossment can be processed with a combination of heat and vacuum, or similar.

The material of the film could be any of the known for current top films and backing layers, such as polyethylene terephthalate (PET), ethylene vinyl acetate (EVA), ethylene butyl acrylate (EBA), polyurethane (PU) or polyvinyl chloride (PVC).

The embossment pattern can have a wide variety of shapes. It can for example have a number of circular grooves as shown in FIG. 1, or it can have a flower-like shape. In another embodiment, not shown, the backing layer can be made of a film with a plastic deformability which is equal to or higher than that of the mouldable adhesive layer.

The invention claimed is:

1. A base plate for an ostomy collection device, comprising:
    a backing layer having an outermost edge and an innermost edge defined by a through-going hole formed through the backing layer; and
    an adhesive layer disposed on a proximal side of the backing layer, the adhesive layer configured for attaching around the stoma of a patient and including an outer adhesive layer and an inner adhesive layer, the outer adhesive layer encircles and continuously contacts an outer perimeter of the inner adhesive layer, and the inner adhesive layer encircles the through-going hole such that the through-going hole is formed through the base plate, a first tan(δ) value of the inner adhesive layer is greater than 1 and higher than a second tan(δ) value of the outer adhesive layer;
    wherein the inner adhesive layer is disposed on a first part of the backing layer and the outer adhesive layer is disposed on a second part of the backing layer, the first part of the backing layer having a combination of less plasticity than the inner adhesive layer, an embossment, and radial extendability when the inner adhesive layer is attached around the stoma, the combination configured to prevent stomal output from the stoma from contacting the inner adhesive layer.

2. A base plate according to claim 1, wherein the first part of the backing layer on which the inner adhesive layer is disposed has a radial length that is longer than a radial length of the second part of the backing layer on which the outer adhesive layer is disposed.

3. A base plate according to claim 1, wherein the embossment includes at least one annular groove encircling the through-going hole.

4. A base plate according to claim 1, wherein the first part of the backing layer on which the inner adhesive layer is disposed is plastically deformable and the second part of the backing layer is elastically deformable.

5. A base plate according to claim 1, wherein a total radial surface distance of the first part of the backing layer on which the inner adhesive layer is disposed is greater than a radial extent of the inner adhesive layer between the innermost edge of the backing layer and the outer perimeter of the inner adhesive layer.

6. A base plate according to claim 1, wherein the second part of the backing layer on which the outer adhesive layer is disposed is not extendable in the radial direction.

7. A base plate for an ostomy collection device, comprising:
  a backing layer having an outermost edge and an innermost edge defined by a through-going hole formed through the backing layer; and
  an adhesive layer disposed on a proximal side of the backing layer, the adhesive layer configured for attaching around the stoma of a patient and including an outer adhesive layer and an inner adhesive layer, the inner adhesive layer formed of a moldable adhesive, the outer adhesive layer encircles and continuously contacts an outer perimeter of the inner adhesive layer, and the inner adhesive layer encircles the through-going hole such that the through-going hole is formed through the base plate, a first $\tan(\delta)$ value of the inner adhesive layer is greater than 1 and higher than a second $\tan(\delta)$ value of the outer adhesive layer;
  wherein the inner adhesive layer is disposed on a first part of the backing layer and the outer adhesive layer is disposed on a second part of the backing layer, the first part of the backing layer including a combination of less plasticity than the inner adhesive layer, an embossment, and radial extendability when attached around the stoma, the combination configured to prevent stomal output from the stoma from contacting the inner adhesive layer.

8. A base plate according to claim 1, wherein the embossment includes a flower-like shape.

* * * * *